US007871983B2

(12) United States Patent
Morishita et al.

(10) Patent No.: US 7,871,983 B2
(45) Date of Patent: *Jan. 18, 2011

(54) REMEDY AND PREVENTIVE FOR DISEASES CAUSED BY NF-κB

(75) Inventors: Ryuichi Morishita, Osaka (JP); Toshio Ogiwara, Minoo (JP); Toshiko Sugimoto, Kyoto (JP); Kazuhiro Maeda, Yamatotakada (JP); Ikuo Kawamura, Hirakata (JP); Toshiyuki Chiba, Nara (JP)

(73) Assignee: Anges MG Inc., Osaka (JP)

( * ) Notice: Subject to any disclaimer, the term of this patent is extended or adjusted under 35 U.S.C. 154(b) by 1712 days.

This patent is subject to a terminal disclaimer.

(21) Appl. No.: 10/366,718

(22) Filed: Feb. 14, 2003

(65) Prior Publication Data

US 2004/0162250 A1 Aug. 19, 2004

Related U.S. Application Data

(63) Continuation of application No. 09/832,841, filed on Apr. 12, 2001, now abandoned, which is a continuation of application No. 08/945,805, filed as application No. PCT/JP96/01234 on May 10, 1996, now Pat. No. 6,262,033.

(30) Foreign Application Priority Data

May 12, 1995 (JP) ................................ 7/114990
Nov. 2, 1995 (JP) ................................ 7/285504

(51) Int. Cl.
*A01N 43/04* (2006.01)
*A61K 31/70* (2006.01)

(52) U.S. Cl. ....................................... 514/44
(58) Field of Classification Search ................ 514/44; 435/6, 325, 375; 536/24.5
See application file for complete search history.

(56) References Cited

U.S. PATENT DOCUMENTS

| 5,591,840 A | 1/1997 | Narayanan et al. |
| 6,262,033 B1 | 7/2001 | Morishita et al. |
| 6,399,376 B1 | 6/2002 | Melford et al. |
| 6,410,516 B1 * | 6/2002 | Baltimore et al. ............. 514/44 |

FOREIGN PATENT DOCUMENTS

| CA | 2102704 | 11/1992 |
| CA | 2131587 | 3/1995 |
| EP | 589330 | 3/1994 |
| EP | 0 824 918 A1 | 2/1998 |
| JP | 6-209778 | 9/1993 |
| JP | 06/508029 | 9/1994 |
| JP | 07/114990 | 5/1995 |
| JP | 07/170998 | 7/1995 |
| JP | 07/285504 | 11/1995 |
| WO | 95/12415 | 5/1995 |
| WO | WO 95/11687 | * 5/1995 |

OTHER PUBLICATIONS

Toshiba Nakajima et al., Involvement of NF-kB Activation in Throwbin-Induced Human Vascular Smooth Muscle Cell Proliferation, Biochem and Biophysical Research Communication, Oct. 1994, p. 950-955, vol. 204, No. 2.

Anna Beilinski et al. Regulation of Gene Expression with Double-Stranded Phosporothioate Oligoonucleotides, Science, Nov. 1990, vol. 250, p. 997-1000.

Sokoloski et al., Antisense Oligonucleotides to the p65 Subnunit of NF-kB Block CD11b Expression and Alter Adhesion Properties of Differentiated HL-60 Granulocytes, Blood, Jul. 1993, vol. 82, No. 2, p. 625-632.

N. Tomita et al., "A Novel Strategy for Gene Therapy and Gene Regulation Analysis Using Transcription Factor Decoy Oligonucleotides", EXP. Nephrol 1997; 5:429-434.

I. Kawamura et al., "Intratumoral Injection of Oligonucleotides to the NFkB Binding Site Inhibits Cachexia In A Mouse Tumor Model", Gene Therapy (1999)6, 91-97.

N. Tomita et al., "Transcription Factor Decoy for Nuclear Factor-κB Inhibits Tumor Necroses Factor-α-Induced Expression of Inteerleukin-6 and Tracellular Adhesion Molecule-1 in Endothelial Cells", Journal of Nypertension 1998, 16:993-1000.

T. Tomita et al., "Suppressed Severity of Collagen-Induced Arthritis by In Vivo Transfection of Nuclear Factor kB Decoy Oligodeoxynucleotides As A Gene Therapy", Arthritis & Rheumatism, vol. 42, No. 12, Dec. 1999.

Kaltschmidt et al., "Transcription factor NF-KB is activated in microglia during experimental autoimmune encephalomyelitis," *J. Neuroimmun.*, 1994, vol. 55: pp. 99-106.

Higgins et al., "Antisense inhibition of the p65 subunit of NF-KB blocks tumorigenicity and causes tumor regression," *PNAS*, Nov. 1993, vol. 90: pp. 9901-9905.

Neish et al., "Functional Analysis of the Human Vascular Cell Adhesion Molecule 1 Promotor," *J. Exp. Med.*, Dec. 1992, vol. 176: pp. 1583-1593.

Menetski, J. Biol. Chem. 275: 7619-25 (2000).

Deok et al., Circ. Res. 90: 1325-32 (2002).

Crinelli et al., Nucl. Acids Res. 30: 2435-43 (2002).

(Continued)

*Primary Examiner*—Sean McGarry
*Assistant Examiner*—Terra Cotta Gibbs
(74) *Attorney, Agent, or Firm*—Foley & Lardner LLP

(57) ABSTRACT

Administration of a decoy, i.e. a compound which specifically antagonizes the nucleic acid domain to which NF-κB is bound, is effective in the treatment and prevention of diseases caused by the transcriptional regulatory factor NF-κB, such as ischemic diseases, inflammatory diseases, autoimmune diseases, cancer metastasis and invasion, and cachexia.

14 Claims, No Drawings

OTHER PUBLICATIONS

Morishita et al., "Oligonucleotide-Based Gene Therapy for Cardiovascular Disease," *Clin. Chem. Lab. Med.*, 1998, vol. 36(8): pp. 529-534.

Nakamura et al., "Prevention and regression of atopic dermatitis by ointment containing NF-κB decoy oligodeoxynucleotides in NC/Nga atopic mouse model," *Gene Therapy*, Sep. 2002, vol. 9, pp. 1221-1229.

Kawamura, et al., "Intravenous injection of oligodeoxynucleotides to the NF-kappaB binding site inhibits hepatic metastasis of M5076 reticulosarcoma in mice," *Gene Therapy*, Jun. 2001, vol. 8(12): 905-12.

Tomita et al., "Inhibition of TNF alpha, induced cytokine and adhesion molecule. Expression in glomerular cells in vitro and in vivo by transcription factor decoy for Exp. Nephrol.," *Exp. Nephrol.*, 2001, vol. 9(3), pp. 181-190.

Tomita et al., "In vivo administration of a nuclear transcription factor-kappaB decoy suppresses experimental crescentic glomerulonephritis," *J. Am. Soc. Nephrol.*, 2000, vol. 11: pp. 1244-1252.

Suzuki et al., "Decoy against nuclear factor-kappa B attenuates myocardial cell infiltration and arterial neointimal formation in murine cardiac allografts," *Gene Therapy*, Nov. 2000, vol. 7(21): pp. 1847-1852.

Tomita et al., "Transcription factor decoy for NFkappaB inhibits cytokine and adhesion molecule expressions in svnovial cells derived from rheumatoid arthritis.," *Rheumatology* (Oxford), Jul. 2000, vol. 39(7): pp. 749-757.

Tomita et al., "Suppressed severity of collagen-induced arthritis by in vivo transfection of nuclear factor kappaB decoy oligodeoxynucleotides as a gene therapy," *Arthritis & Rheum..* 1999, vol. 42, pp. 2532-2542.

Matsushita et al., "Hypoxia-induced endothelial apoptosis through nuclear factor-kappaB (NF-kappaB)-medicated bcl-2 suppression: in vivo evidence of the importance of NF-kappaB in endothelial cell regulation," *Circulation Res.*, May 2000, vol. 86(9): pp. 974-981.

Sawa et al., Circulation, 96 (Supp. II) 280-84 (1997).

Kawamura et al., "Intratumoral injection of oligonucleotides to the NF kappa B binding site inhibits cachexia in a mouse tumor model," *Gene Therapy*, Jan. 1999, vol. 6(1): pp. 91-97.

Tomita et al., "Transcription factor decoy for nuclear factor-kappaB inhibits tumor necrosis factor-alpha-induced expression of interleukin-6 and intracellular adhesion molecule-1 in endothelial cells," *J. Hypertension*, Jul. 1998, vol. 16: pp. 993-1000.

Morishita et al., "In vivo transfection of cis element "decoy" against nuclear factor-kappaB binding site prevents myocardial infarction," *Nature Med.*, Aug. 1997, vol. 3(8): pp. 894-899.

Nakajima, et al., "Involvement of NF-KB Activation in Thrombin Induced Human Vascular Smooth Muscle Cell Proliferation," *Biochem. Biophys*, Oct. 1994, vol. 204(2): pp. 950-955.

Sawa, et al., "A Novel Strategy for Myocardial Protection Using in Vivo Transfection of CIS Element "Decoy" Against NFκB Binding Site," *Circulation*, Nov. 1997, vol. 96(9), pp. 11-281-11-285.

Morishita, et al., "Application of Transcription Factor "Decoy" Strategy As Means of Gene Therapy and Study of Gene Expression Cardiovascular Disease," *Cir. Res.*, 1998, vol. 82, pp. 1023-1028.

\* cited by examiner

REMEDY AND PREVENTIVE FOR DISEASES CAUSED BY NF-κB

This application is a continuation of 09/832,841, filed Apr. 12, 2001, now abandoned, which application is a continuation of application Ser. No. 08/945,805, filed Jan. 6, 1998, now U.S. Pat. No. 6,262,033, which application is the national phase of PCT/JP96/01234, filed May 10, 1996, published in a non-English language.

TECHNICAL FIELD

The present invention relates to the prevention and treatment of various diseases associated with NF-κB which is known to be a regulatory factor in the transcription of cytokines and adhesion factors. More particularly, the invention relates to an NF-κB decoy, a composition comprising said decoy for the therapy and prophylaxis of NF-κB-associated diseases, and a method for said therapy and prophylaxis.

BACKGROUND ART

A variety of diseases including asthma, cancers, heart diseases, autoimmune diseases, and viral infections manifest varying symptoms and signs and yet it has been suggested that either an overexpression or underexpression of one or a few proteins is a major etiologic factor in many cases. Moreover, a variety of transcriptional regulatory factors such as transcription activators and transcription inhibitors are involved in the expression of proteins. NF-κB, a substance known to be one of such transcriptional regulatory factors, is a heterodimer of p65 and p50 proteins. In the cytoplasm, NF-κB is usually present as substance binding with IκB, an inhibition factor, and thereby prevented from migrating into the nucleus. However, when cell is stimulated by cytokines, ischemia, or reperfusion for whatever reason, IκB is phosphorylated and decomposed so that the NF-κB is activated and penetrates into the nucleus. NF-κB attaches itself to the NF-κB binding site of the chromosome and then promotes transcription of the gene located at downstreams. The gene controlled by NF-κB includes cytokines such as IL-1, IL-6, IL-8, etc. and adhesion factors such as VCAM-1, ICAM-1, etc. . .

DISCLOSURE OF THE INVENTION

Predicting that stimulation of the production of those cytokines and adhesion factors is causative of various morbidities such as ischemic diseases, inflammatory diseases, autoimmune diseases, cancer metastasis and invation, and cachexia, the inventors of this invention did much research and found that it is a rewarding therapeutic approach to suppress expression of those genes which are activated by NF-κB by administering a decoy of the NF-κB binding site of chromosome, that is to say a compound which specifically antagonizes the, binding site of chromosome to which NF-κB is conjugated. The present invention has been developed on the basis of the above finding.

The present invention, therefore, provides a pharmaceutical composition comprising an NF-κB decoy as an active ingredient for the therapy and prophylaxis of various NF-κB-associated diseases and a method for said therapy and prophylaxis.

The diseases in which the therapeutic/prophylactic composition of the invention is indicated are NF-κB-associated diseases, that is to say diseases caused by the unwanted activation of genes under control of the transcriptional regulatory factor NF-κB, and among such diseases can be reckoned ischemic diseases, inflammatory diseases, autoimmune diseases, cancer metastasis and invasion, and cachexia. The ischemic disease includes ischemic diseases of organs (e.g. ischemic heart diseases such as myocardial infarction, acute heart failure, chronic heart failure, etc., ischemic brain diseases such as cerebral infarction, and ischemic lung diseases such as palmonary infarction), aggravation of the prognosis of organ transplantation or organ surgery (e.g. aggravation of the prognosis of heart transplantation, cardiac surgery, kidney transplantation, renal surgery, liver transplantation, hepatic surgery, bone marrow transplantation, skin grafting, corneal transplantation, and lung transplantation), reperfusion disorders, and post-PTCA restenosis. The inflammatory disease mentioned above includes various inflammatory diseases such as nephritis, hepatitis, arthritis, etc., acute renal failure, chronic renal failure, and arteriosclerosis, among other diseases. The autoimmune disease mentioned above includes but is not limited to rheumatism, multiple sclerosis, and Hashimoto's thyroiditis. Particularly the pharmaceutical composition containing the NF-κB decoy according to the present invention as an active ingredient is very suited for the therapy and prophylaxis of reperfusion disorders in ischemic diseases, aggravation of the prognosis of organ transplantation or organ surgery, post-PTCA restenosis, cancer metastasis and invasion, and cachexia such as weight loss following the onset of a cancer.

The NF-κB decoy that can be used in the present invention may be any compound that specifically antagonizes the NF-κB binding site of the chromosome and includes but is not limited to nucleic acids and their analogs. As preferred examples of said NF-κB decoy, there can be mentioned oligonucleotides containing the nucleotide sequence of GGGATTTCCC (the sequence from the 8th through the 17th nucleotides from the 5'-end of SEQ ID NO: 1 in Sequence Listing) or its complementary sequence, muteins thereof, and compounds containing any of them within the molecule. The oligonucleotides may be DNAs or RNAs, and may contain modified nucleotides and/or pseudonucleotides. Furthermore, those oligonucleotides, variants thereof, or compounds containing any of them may be single-stranded or double-stranded and linear or cyclic. The variants are those involving mutations such as substitution, addition and/or deletion of any part of the above-mentioned sequence, and mean nucleic acids specifically antagonizing the binding site of chromosome to which NF-κB is conjugated. The more preferred NF-κB decoy includes double-stranded oligonucleotides each containing one or a plurality of the above nucleotide sequence and variants thereof. The oligonucleotide which can be used in the present invention includes oligonucleotides modified so as to be less susceptible to biodegradation, such as those oligonucleotides containing the thiophosphoric diester bond available upon substitution of sulfur for the oxygen of the phosphoric diester moiety (S-oligo) and those oligonucleotides available upon substitution of a methyl phosphate group carrying no electric charge for the phosphoric diester moiety.

Regarding to a technology for producing the NF-κB decoy for use in the present invention, the conventional chemical or biochemical methods for synthesis can be utilized. When a nucleic acid, for instance, is to be used as the NF-κB decoy, the methods for nucleic acid synthesis which are commonly used in genetic engineering can be employed. For example, the objective decoy oligonucleotide can be directly synthesized on a DNA synthesizer. Or a nucleic acid or its fragments, each synthesized beforehand, can be amplified by PCR or using a cloning vector or the like. Furthermore, the desired nucleic acid can be obtained by such procedures as cleavage with restriction enzymes or the like and/or ligation by means of DNA ligase or the like. In order to obtain a decoy nucleotide which is more stable within cells, the base, sugar or/and phosphoric acid moieties of the nucleic acid may be alkylated, acylated, or otherwise chemically modified.

The pharmaceutical composition containing the NF-κB decoy as an active ingredient according to the present invention is not limited in form only if the active ingredient may be taken up by the cells in the affected site or the cells of the target tissue. Thus, the NF-κB decoy, either alone or in admixture with the common pharmaceutical carrier, can be administered orally, parenterally, topically or externally. The pharmaceutical composition may be provided in liquid dosage forms such as solutions, suspensions, syrups, liposomes, lotions, etc. or in solid dosage forms such as tablets, granules, powders, and capsules. Where necessary, those pharmaceutical compositions may be supplemented with various vehicles, excipients, stabilizers, lubricants, and/or other conventional pharmaceutical additives, such as lactose, citric acid, tartaric acid, stearic acid, magnesium stearate, terra alba, sucrose, cornstarch, talc, gelatin, agar, pectin, peanut oil, olive oil, caccao butter, ethylene glycol, and so on.

Particularly when a nucleic acid or a modification product thereof is used as the NF-κB decoy, the preferred dosage form includes those which are generally used in gene therapy, such as liposomes inclusive of membrane fusion liposomes utilizing Sendai virus and liposomes utilizing endocytosis, preparations containing cationic lipids such as Lipofectamine (Life Tech Oriental) or virosomes utilizing a retrovirus vector, adenovirus vector, or the like. Particularly preferred are membrane fusion liposomes.

The structure of such a liposomal preparation may be any of a large unilamellar vesicle (LUV), a multi-lamellar vesicle (MLV), and a small unilamellar vesicle (SUV). The approximate size of vesicles may range from 200 to 1000 nm for LUV, from 400 to 3500 nm for MLV, and from 20 to 50 nm for SUV but in the case of a membrane fusion liposomal preparation using Sendai virus, for instance, MLV with a vesicular system of 200-1000 nm in diameter is preferably employed.

There is no limitation on the technology for liposome production only if the decoy can be successfully entrapped in vesicles. Thus, such liposomes can be manufactured by the conventional techniques such as the reversed phase evaporation method (Szoka, F., et al: Biochim. Biophys. Acta, Vol. 601 559 (1980)), ether injection method (Deamer, D. W.: Ann. N.Y. Acad. Sci., Vol. 308 250 (1978)), and surfactant method (Brunner, J., et al: Biochim. Biophys. Acta, Vol. 455 322 (1976)), to name but a few examples.

The lipid that can be used for constructing a liposomal structure includes phospholipids, cholesterol and its derivatives, and nitrogen-containing lipids but phospholipids are generally preferred. The phospholipid that can be used includes naturally-occurring phospholipids such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, lysolecithin, etc., the corresponding phospholipids hydrogenated by the conventional method, and synthetic phospholipids such as dicetyl phosphate, distearoylphosphatidylcholine, dipalmitoylphosphatidylcholine, dipalmitoylphosphatidylethanolamine, dipalmitoylphosphatidylserine, eleostearoylphosphatidylcholine, eleostearoylphosphatidylethanolamine, eleostearoylphosphatidylserine, and so on.

The lipids inclusive of phospholipids can be used each alone or in a suitable combination. By using a lipid containing a positively-charged atomic group such as ethanolamine or choline within the molecule, the binding rate of an electrically negative decoy nucleotide can be enhanced. In addition to the principal phospholipid, various compounds such as cholesterol and its derivatives, stearylamine, -tocopherol, etc., which are known as liposome additives, can be added in the manufacture of liposomes.

To the resulting liposomes can be added a membrane fusion promoter such as Sendai virus, inactivated Sendai virus, a membrane fusion promoting protein purified from Sendai virus, polyethylene glycol, or the like can be added for assisting in the intracellular uptake by the cells at the affected site or of the target tissue.

A typical procedure for the production of pharmaceutical liposomes is now described in detail. The above-mentioned liposome-forming substance as well as cholesterol or the like is dissolved in an organic solvent such as tetrahydrofuran, chloroform, ethanol, or the like. In a suitable vessel, the solvent is distilled off under reduced pressure to leave a film of the liposome-forming substance on the inside wall of the vessel. Then, a buffer containing the NF-κB decoy is added and the mixture is stirred. After optional addition of said membrane fusion promoter, the liposomes are isolated. The liposomes in which the NF-κB decoy has thus been entrapped are suspended in a suitable medium or a lyophilizate thereof is redispersed in a suitable medium for use in therapy. The membrane fusion promoter may be added in the interim period after isolation of the liposomes and before use.

There is no limitation on the decoy content of the pharmaceutical composition containing the NF-κB decoy as an active ingredient only if the decoy is contained in amounts effective to control NF-κB-associated diseases. Thus, the decoy content can be liberally selected according to the disease to be controlled, the target site, dosage form, and dosage schedule.

The pharmaceutical composition containing the NF-κB decoy as an active ingredient as provided in the above manner can be administered by various methods according to the type of disease and the kind of decoy contained. Taking ischemic diseases, inflammatory diseases, autoimmune diseases, cancer metastasis or invasion, and cachexia as examples, the composition can be infused intravascularly, applied directly to the affected area, injected into the lesion, or administered into the regional blood vessel in the affected region. As a further specific example, when PTCA is performed for infarction of an organ, the pharmaceutical composition can be administered into the local blood vessel concurrently with the operation or pre- and postoperatively. For organ transplantation, the graft material can be previously treated with the composition of the invention. Furthermore, in the treatment of osteoarthritis or rheumatism, the composition can be directly injected into the joint.

The dosage of the NF-κB decoy is selected with reference to the patient's age and other factors, type of disease, the kind of decoy used, etc. but for intravascular, intramuscular, or intraarticular administration, for instance, a unit dose of 10-10,000 nmoles can generally be administered once to a few times daily.

BEST MODE FOR CARRYING OUT THE INVENTION

The following examples are intended to describe the present invention in further detail.

EXAMPLE 1

Synthesis of an NF-κB Decoy (Decoy Oligonucleotide)

On a DNA synthesizer, an NF-κB decoy oligonucleotide and a scrambled decoy oligonucleotide (an oligonucleotide having the same base composition as the NF-κB decoy oligonucleotide but a randomized sequence), the nucleotide sequences of which are shown below, were respectively synthesized from S-oligonucleotides. Those nucleotides were heated at 80° C. for 30 minutes and then allowed to cool to room temperature over 2 hours to provide double-stranded DNAs.

NF-κB decoy oligonucleotide

```
CCTTGAAGGGATTTCCCTCC (SEQ ID NO: 1)

GGAACTTCCCTAAAGGGAGG (SEQ ID NO: 3)
```

Scrambled decoy oligonucleotide

```
TTGCCGTACCTGACTTAGCC (SEQ ID NO: 2)

AACGGCATGGACTGAATCGG (SEQ ID NO: 4)
```

EXAMPLE 2

Production of Liposomal Preparations

Phosphatidylserine, phosphatidylcholine, and cholesterol, provided in a weight ratio of 1:4.8:2 (a total of 10 mg), were dissolved in tetrahydrofuran. Using a rotary evaporator, the tetrahydrofuran was removed from the lipid solution to leave the lipid in the form of a film adherent to the flask wall. To this was added 200 ml of saline (BSS; 139 mM NaCl, 5.4 mM KCl, 10 mM Tris-HCl, pH 7.6) containing the NF-κB decoy oligonucleotide (0.7 mg) prepared in Example 1 and the mixture was stirred and sonicated under the usual conditions to provide a suspension of liposomes containing the NF-κB decoy oligonucleotide. This suspension of liposome vesicles (0.5 ml, lipid content 10 mg) was mixed with purified Sendai virus (Z strain, 10000 hemaglutinating units) exposed to UV radiation (110 erg/mm$^2$/sec) 3 minutes before use and the mixture was made up to 4 ml with BSS. This mixture was held at 4° C. for 5 minutes and, then, subjected to gentle shaking at 37° C. for 30 minutes. After the Sendai virus not bound to the liposomes was removed by sucrose density gradient centrifugation, the uppermost layer was separated and its concentration was adjusted with BSS to provide a liposomal preparation containing 8 μM NF-κB decoy oligonucleotide as entrapped. A liposomal preparation was similarly produced using the scrambled decoy oligonucleotide of Example 1 in lieu of the NF-κB decoy oligonucleotide.

EXAMPLE 3

A Reperfusion Model Experiment (1) Method

After 9~10-week-old SD rats were anesthetized with pentobarbital sodium, a cannula was inserted into the left carotid artery adjacent to the airway and indwelled near the aortic valve of the heart (close to the ostium of the coronary artery). In addition, the trachea was cannulated and the animal was placed on supportive respiration by connecting the tracheal cannula to an artificial respirator. Thereafter, a left intercostal incision was made and the left descending anterior branch of the rat heart was ligated to produce ischemia. After 30 minutes, the ligating suture was cut to start reperfusion. Immediately thereafter, 1.5 ml/rat of the liposomally entrapped NF-κB decoy nucleotide or scrambled decoy nucleotide prepared in Example 2 was administered via the cannula indwelled close to the ostium of the coronary artery. After the chest was closed, the trachea was also sutured and the animal was kept alive. After 24 hours, the rat was reanesthetized and the heart was enucleated and washed with saline. The ventricle of the rat heart was sliced into six sections which were stained with tetrazolium chloride (TTC). The six sections were respectively photographed and subjected to image analysis. The infarcted area was calculated by means of the following equation.

Infarction rate (%)= the sum of infarct areas of 6 sections/the sum of areas of 6 sections×100

Statistical analysis was made by multiple comparison (ANOVA).

(2) Results

The results are presented in Table 1. In the untreated control group and the scrambled decoy treatment group, myocardial infarcts were found in approximately equal degrees. In the group given the NF-κB decoy nucleotide, the infarct was suppressed to 19% with a significant difference (P<0.01) from the untreated group and the scrambled decoy group.

TABLE 1

|  | NF-κB decoy nucleotide group | Scrambled decoy group | Untreated group |
|---|---|---|---|
| Myocardial infarct area/ total area | 19 2% | 28 1% | 28 1% |

A similar inhibitory effect was found when the liposomes were administered immediately before induction of infarction.

EXAMPLE 4

Inhibition of Cancer Metastasis (1) Method

To 7-week-old female mice of the C57BL/6 strain, 1×10$^4$ murine reticulum cell sarcoma M5076 cells were administered intravenously and 24 hours later 0.2 ml (6 nmoles) of an NF-κB decoy nucleotide prepared in the same manner as Example 2 was administered intravenously. A control group received 0.2 ml of saline in the same manner. On day 14 after intravenous administration of M5076, the animal was autopsied and the number of tumor nodules on the surface of the liver was counted under the stereoscopic microscope. Each group consisted of 10 mice. For statistical analyses, Kruskal-Wallis test and Dunnett's multiple comparison were used.

(2) Results

Whereas the mean number of tumor nodules in the control group was 166 with a median value of 173 (116-198), the NF-κB decoy treatment group showed a mean number of 29 and a median number of 27 (19-54). Thus, between the NF-κB decoy treatment group and the control group, a significant difference was found at the 1% level.

EXAMPLE 5

Inhibition of Cachexia (1) Method

Using 7-week-old male BALB/c mice, a 2 mm cubic tumor mass of murine colon cancer line Colon 26 was transplanted subdermally. Beginning day 7 after transplantation, 0.2 ml (6 nmoles) of the NF-κB decoy or the scrambled decoy was administered into the tumor mass and the body weight and tumor weight were serially determined. The animal was autopsied on day 13 and the epididymal fat and gastrocnemius muscle were isolated and weighed. Furthermore, the wet carcass weight exclusive of all the remaining organs and tumor was determined. The tumor weight was calculated from the major and minor diameters of each tumor mass by means of the following equation.

Tumor weight (mg)= major diameter×minor diameter$^2$/2

Each group consisted of 10 mice. Statistical analyses were made by ANOVA in one-way layout and Dunnett's multiple comparison.

(2) Results

In the tumor-bearing group, growth of the tumor resulted in significant decreases in body weight, epididymal fat weight, gastrocnemius muscle weight, and wet carcass weight. In the NF-κB decoy group, improvements were obtained, amounting to 47% for body weight, 42% for epididymal fat weight, 60% for gastrocnemius weight, and 52% for wet carcass weight. However, no improvement was found in the scrambled decoy group. There was no definite effect on tumor weight.

What is claimed:

1. A method of treating or preventing an NF-κB-associated disease which comprises administering to a human an effective amount of a pharmaceutical composition comprising a polynucleotide NF-κB chromosomal binding site decoy which antagonizes NF-κB-mediated transcription of a gene located downstream of said binding site, wherein the polynucleotide comprises nucleotides 8-17 of SEQ ID NO:1.

2. A method for treatment of an NF-κB-associated which comprises administering to an animal an effective amount of a polynucleotide NF-κB chromosomal binding site decoy which antagonizes NF-κB-mediated transcription of a gene located downstream of a NF-κB binding sit; wherein said polynucleotide comprises nucleotides 8-17 of SEQ ID NO:1.

3. The method according to claim 2 wherein the NF-κB-associated disease is selected from the group consisting of: an ischemic disease, an inflammatory disease, and an autoimmune disease.

4. The method according to claim 2 wherein the NF-κB-associated disease is an ischemic disease.

5. The method according to claim 2 wherein the NF-κB-associated disease is selected from the group consisting of: a reperfusion disorder in ischemic disease, aggravation of a prognosis of an organ transplantation, aggravation of a prognosis of an organ surgery, and a post-PTCA restinosis.

6. The method according to claim 2 wherein the NF-κB-associated disease is selected from the group consisting of: a reperfusion disorder in ischemic heart disease, aggravation of a prognosis of a heart transplantation, aggravation of a prognosis of a heart surgery, and post PTCA restinosis.

7. The method according to claim 2 wherein the NF-κB-associated disease is selected from the group consisting of: a cancer metastasis, a cancer invasion, and cachexia.

8. The method according to claim 2, wherein the polynucleotide consists essentially of nucleotides 8-17 of SEQ ID NO:1.

9. The method according to claim 1, wherein the NF-κB-associated disease is selected from the group consisting of: an ischemic disease, an inflammatory disease, and an autoimmune disease.

10. The method according to claim 1, wherein the NF-κB-associated disease is an ischemic disease.

11. The method according to claim 1, wherein the NF-κB-associated disease is selected from the group consisting of: a reperfusion disorder in ischemic disease, aggravation of a prognosis of an organ transplantation, aggravation of a prognosis of an organ surgery, and a post-PTCA restinosis.

12. The method according to claim 1, wherein the NF-κKB-associated disease is selected from the group consisting of: a reperfusion disorder in ischemic heart disease, aggravation of a prognosis of a heart transplantation, aggravation of a prognosis of a heart surgery, and post PTCA restinosis.

13. The method according to claim 1, wherein the NF-κB-associated disease is selected from the group consisting of: a cancer metastasis, a cancer invasion, and cachexia.

14. The method according to claim 1, wherein the polynucleotide consists essentially of nucleotides 8-17 of SEQ ID NO:1.

* * * * *

UNITED STATES PATENT AND TRADEMARK OFFICE
CERTIFICATE OF CORRECTION

| | | |
|---|---|---|
| PATENT NO. | : 7,871,983 B2 | Page 1 of 1 |
| APPLICATION NO. | : 10/366718 | |
| DATED | : January 18, 2011 | |
| INVENTOR(S) | : Morishita et al. | |

It is certified that error appears in the above-identified patent and that said Letters Patent is hereby corrected as shown below:

IN THE SPECIFICATION

Column 2, Line 8: Please replace "palmonary" with -- pulmonary --.

IN THE CLAIMS

Claim 2, Column 9, Line 9: Please replace "associated which" with -- associated disease which --.

Claim 2, Column 9, Line 13: Please replace "binding sit" with -- binding site --.

Claim 5, Column 9, Line 25: Please replace "restinosis" with -- restenosis --.

Claim 6, Column 9, Line 30: Please replace "restinosis" with -- restenosis --.

Claim 11, Column 10, Line 17: Please replace "restinosis" with -- restenosis --.

Claim 12, Column 10, Line 22: Please replace "restinosis" with -- restenosis --.

Signed and Sealed this
Sixteenth Day of August, 2011

David J. Kappos
*Director of the United States Patent and Trademark Office*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
ccttgaaggg atttccctcc                                             20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
ttgccgtacc tgacttagcc                                             20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
ggaacttccc taaagggagg                                             20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
aacggcatgg actgaatcgg                                             20
```